US008946190B2

(12) United States Patent
Gagnon et al.

(10) Patent No.: US 8,946,190 B2
(45) Date of Patent: Feb. 3, 2015

(54) MEDIUM-CHAIN LENGTH FATTY ACIDS, SALTS AND TRIGLYCERIDES IN COMBINATION WITH GEMCITABINE FOR TREATMENT OF PANCREATIC CANCER

(75) Inventors: Lyne Gagnon, Laval (CA); Lilianne Geerts, St-Lazare (CA); Christopher Penney, Pierrefonds (CA)

(73) Assignee: Prometic Biosciences Inc., Mont-Royal, Quebec (CA)

( * ) Notice: Subject to any disclaimer, the term of this patent is extended or adjusted under 35 U.S.C. 154(b) by 517 days.

(21) Appl. No.: 12/809,380

(22) PCT Filed: Dec. 18, 2008

(86) PCT No.: PCT/CA2008/002190
§ 371 (c)(1),
(2), (4) Date: Jul. 8, 2010

(87) PCT Pub. No.: WO2009/076761
PCT Pub. Date: Jun. 25, 2009

(65) Prior Publication Data
US 2010/0273731 A1  Oct. 28, 2010

Related U.S. Application Data

(60) Provisional application No. 61/008,129, filed on Dec. 19, 2007.

(51) Int. Cl.
| A61K 31/7068 | (2006.01) |
| A61K 31/517 | (2006.01) |
| A61K 31/23 | (2006.01) |
| A61K 31/20 | (2006.01) |
| A61P 35/00 | (2006.01) |

(52) U.S. Cl.
CPC ............. *A61K 31/23* (2013.01); *A61K 31/20* (2013.01); *A61K 31/517* (2013.01); *A61K 31/7068* (2013.01)
USPC ......................................................... 514/49

(58) Field of Classification Search
CPC ..... A61K 31/20; A61K 31/23; A61K 31/517; A61K 31/7068; A61K 2300/00
See application file for complete search history.

(56) References Cited

U.S. PATENT DOCUMENTS

| 2003/0049302 A1 | 3/2003 | Pauletti et al. |
| 2006/0128800 A1* | 6/2006 | Penney et al. ................ 514/517 |

FOREIGN PATENT DOCUMENTS

| WO | WO 02/083120 A2 | 10/2002 |
| WO | WO 2004/069237 A1 | 8/2004 |

OTHER PUBLICATIONS

Moore, M. J. et al., Journal of Clinical Oncology, "Erlotinib Plus Gemcitabine Compared with Gemcitabine Alone in Patients With Advanced Pancreatic Cancer: A Phase III Trial of the National Cancer Institute of Canada Clinical Trials Group", published Apr. 2007, vol. 25, No. 15, pp. 1960-1966.*
Nkondjock, A. et al., British Journal of Cancer, "Specific fatty acid intake and the risk of pancreatic cancer in Canada", 2005, vol. 92, pp. 971-977.*
Falconer et al., "Effect of Eicosapentaenoic Acid and Other Fatty Acids on the Growth in vitro of Human Pancreatic Cancer Cell Lines," Br. J. Cancer 69:826-832, 1994.
Hering et al., "Inhibition of Proliferation by Omega-3 Fatty Acids in Chemoresistant Pancreatic Cancer Cells," Ann. Surg. Oncol. 14:3620-3628, 2007.
International Preliminary Report on Patentability from International Application No. PCT/CA2008/002190, dated Jun. 22, 2010 (date of issuance of report) and Jul. 1, 2010 (date of mailing of report).
Hidalgo, "Pancreatic cancer," N Engl J Med. 362(17):1605-17 (2010).
Lawrence, "Pancreatic cancer: Progress lacking," HemOnc Today. <http://www.healio.com/hematology-oncology/gastrointestinal-cancer/news/print/hematology-oncology/%7Bb7b3f61f-9e18-43cb-8614-63370cff4e3b%7D/pancreatic-cancer-progress-lacking>, published on Sep. 25, 2008, retrieved on Aug. 12, 2014 (6 pages).
"Pancreatic Cancer Overview," American Cancer Society. Last medical review on Aug. 1, 2014 (35 pages).

* cited by examiner

*Primary Examiner* — Layla Bland
*Assistant Examiner* — Bahar Craigo
(74) *Attorney, Agent, or Firm* — Clark & Elbing LLP (57) ABSTRACT

The present invention relates to the use of medium-chain length fatty acids of formula I, triglycerides of formula 2 (wherein n=6-10), salts thereof, or mixtures thereof, in combination with gemcitabine and optionally erlotinib in the treatment of pancreatic cancer in human patients. Exemplary medium-chain length fatty acid/triglyceride compounds include capric acid, sodium caprate, tricaprin, lauric acid, sodium laurate, and trilaurin.

$$H_3C(CH_2)_nCOX \quad \text{I}$$

$$H_3C(CH_2)_nCO-\begin{matrix}-OC(CH_2)_nCH_3\\-OC(CH_2)_nCH_3\end{matrix} \quad \text{II}$$

14 Claims, 4 Drawing Sheets

MEDIUM-CHAIN LENGTH FATTY ACIDS, SALTS AND TRIGLYCERIDES IN COMBINATION WITH GEMCITABINE FOR TREATMENT OF PANCREATIC CANCER

CROSS-REFERENCE TO RELATED APPLICATIONS

This application is the U.S. national stage filing under 35 U.S.C. §371 of international application PCT/CA2008/002190, filed Dec. 18, 2008, which claims benefit of U.S. Provisional Patent Application No. 61/008,129, filed Dec. 19, 2007.

RELATED APPLICATION

The present application claims priority of U.S. application Ser. No. 61/008,129 filed on Dec. 19, 2007, the content of which is incorporated herein by reference in its entirety.

FIELD OF INVENTION

The present invention relates to the treatment of cancers. More particularly, the invention relate to methods, compounds, and compositions for the treatment of pancreatic cancer in a human patient.

BACKGROUND OF INVENTION

Cancer refers to more than one hundred clinically distinct forms of the disease. Almost every tissue of the body can give rise to cancer and some can even yield several types of cancer. Cancer is characterized by an abnormal growth of cells which can invade the tissue of origin or spread to other sites. In fact, the seriousness of a particular cancer, or the degree of malignancy, is based upon the propensity of cancer cells for invasion and the ability to spread. That is, various human cancers (e.g., carcinomas) differ appreciably as to their ability to spread from a primary site or tumor and metastasize throughout the body. Indeed, it is the process of tumor metastasis which is detrimental to the survival of the cancer patient. A surgeon can remove a primary tumor, but a cancer that has metastasized often reaches too many places to permit a surgical cure. To successfully metastasize, cancer cells must detach from their original location, invade a blood or lymphatic vessel, travel in the circulation to a new site, and establish a tumor.

The twelve major cancers are prostate, breast, lung, colorectal, bladder, non-Hodgkin's lymphoma, uterine, melanoma, kidney, leukemia, ovarian, and pancreatic cancers. Generally, four types of treatment have been used for the treatment of metastatic cancers: surgery, radiation therapy, chemotherapy, and immunotherapy. Surgery may be used to remove the primary tumor and/or to improve the quality of life by removing a metastasis, for example, that is obstructing the gastrointestinal tract. Radiation therapy may also be used for treatment of a primary tumor where it is difficult to surgically remove the entire tumor and/or to treat cutaneous and/or lymph node metastasis. A number of chemotherapeutic drugs are available for the treatment of cancer and most often the treatment regimen calls for a combination of these drugs, primarily to deal with the phenomena of drug resistance. That is, the biochemical process which develops over time whereby the cancer is no longer responsive, or becomes refractory, to a particular chemotherapeutic drug prior to eradication of the cancer. Immunotherapy is mostly limited to the use of cytokines or therapeutic cancer vaccines. These treatments have also met with limited success. Treatment with cytokines is limited by life threatening toxicity. Treatment with cancer vaccines is initially promising but with time the tumor usually develops immune tolerance, often by an alteration in phenotypic antigen expression to which the vaccine responds. Indeed, the four types of treatment for cancer noted above all have serious limitations: surgery (the inability to completely remove extensive metastasis), radiation (the inability to selectively deliver radiation to cancer cells), chemotherapy (the inability to selectively kill cancer cells in the presence of rapidly proliferating normal cells), and immunotherapy (noted above). For this reason, other newer therapeutic approaches are under exploration (e.g., kinase inhibitors, antiangiogenesis agents, gene therapy) but these treatments are, relatively speaking, in their infancy. Therefore, a need still exists for novel compounds (e.g., a non-cytotoxic, chemotherapeutic drug), which are efficacious (e.g., reduction of tumor size or spread of metastases) and have reduced toxicity and can be used either alone or in combination with standard chemotherapeutic drugs, for the treatment of cancers which include pancreatic cancer.

Pancreatic cancer is a malignant tumor within the pancreatic gland. The pancreatic gland, or pancreas, is a large elongated gland which lies behind the stomach. The external or exocrine secretions of the pancreas contain digestive enzymes necessary for the processing (breakdown) of food. An internal or endocrine secretion, insulin, is produced by the beta cells of the pancreas while another internal secretion, glucagon, is produced by the alpha cells of the pancreas. Insulin reduces the amount of sugar in the blood while glucagon increases blood sugar. The exocrine and endocrine cells of the pancreas form completely different types of tumors. Exocrine tumors constitute the most common type of pancreatic cancer. Although benign (non-cancerous) cysts and benign tumors (cystadenomas) can occur, most pancreatic exocrine tumors are malignant of which approximately 95% are adenocarcinomas. Patients diagnosed with pancreatic cancer typically have a poor prognosis primarily because the cancer usually causes no symptoms until metastasis of the primary tumor takes place. Median survival from diagnosis of the cancer is approximately three to six months while five-year survival is significantly less than 5%.

Treatment of pancreatic cancer depends upon the stage or extent of the disease. Radical pancreaticoduodenectomy is currently the only chance of cure, especially for minimal disease. Although chemotherapy yields some improvement in survival of patients with locally advanced disease, the overall effect is small. Also, surgery or radiotherapy of locally advanced unresectable pancreatic cancer does not lead to significantly prolonged survival. Pancreatic cancer patients have approximately a 3% chance of survival beyond one year after metastasis (e.g., first diagnosis of cancer) occurs. This rate or survival increases to 18% upon treatment with the cytotoxic drug gemcitabine (Gemzar™) and gemcitabine is the standard first line therapy for pancreatic cancer. Gemcitabine is a vicinol difluorine substituted deoxycytidine analogue which functions as an antimetabolite chemotherapeutic drug. As such, gemcitabine suffers the two significant limitations noted above for chemotherapeutic drugs in general; toxicity arising from a lack of specificity between cancer cells and rapidly dividing normal cells and the eventual development of drug resistance. More recently, approval has been given to treatment of metastatic pancreatic cancer with the combination of erlotinib (Tarceva™) and gemcitabine. However, the one-year survival for pancreatic cancer patients increases only from 18% for treatment with gemcitabine alone to 24% with combination gemcitabine and erlotinib.

Erlotinib is a low molecular weight synthetic inhibitor of the epidermal growth factor receptor tyrosine kinase and so belongs to the newer class of drugs, kinase inhibitors, noted above. However, like cytotoxic drugs, the kinase inhibitors are quite toxic due to the inability to distinguish between cancer cells and rapidly dividing normal cells and they are prone to develop resistance with prolonged use.

In view of the above, there is a strong need for new approaches of cancer treatment wherein efficacy of the chemotherapeutic drug is increased and its toxicity is decreased. More particularly, there is a need for the treatment of metastatic pancreatic cancer because its prognosis is poor and the only few treatment options available include the use of highly toxic drugs which lose their efficacy with time. There is thus an urgent need for new approaches exemplified by a novel treatment regimen consisting of a novel combination of drugs yielding unanticipated efficacy (e.g., reduction in tumor size or spread of metastasis) while resulting in limited toxicity in order to provide a significant improvement in the otherwise abysmal outcome for pancreatic cancer patients.

The Applicant is aware of the followings references which may suggest a link between medium-chain length fatty acids and antitumor activity: Tolnai et al., Can. J. Biochem. Physiol. 39:713-719, 1961; Tolnai et al., Can. J. Biochem. Physiol. 40:1367-1373, 1962; Tolnai et al. Can. J. Biochem. 44:979-981, 1966; Nishikawa et al. Chem. Pharm. Bull. Tokyo 24:387-393, 1976; Burton et al. Am. J. Clin. Nutr. 53:10825-10865, 1991; U.S. Pat. No. 5,081,105; Colquhoun et al., Gen. Pharmac. 30:191-194, 1998; and Falconer et al., Br. J. Cancer 69:826-832, 1994. However it was unknown prior to the present invention that medium-chain length fatty acids, metallic salts or triglycerides thereof may be effective for the treatment of pancreatic cancer.

The present invention addresses the two limitations noted hereinabove that arise with commonly used commercial chemotherapeutic agents, i.e. drug toxicity and drug resistance by providing novel methods, compounds, and compositions for the treatment of pancreatic cancer in a human patient.

Additional features of the invention will be apparent from review of the disclosure, drawings and description of the invention below.

BRIEF SUMMARY OF THE INVENTION

The present invention relates to compounds, compositions and treatment regimens for the treatment of pancreatic cancer in humans. Particular aspects of the invention relates to use of medium-chain length fatty acids, their salts, their triglycerides or mixtures thereof in the treatment of pancreatic cancer.

One particular aspect of the invention concerns the use of a compound represented by Formula I or Formula II:

wherein n is 6-10 and X is hydrogen, a metallic monocationic counterion or a dicationic counterion;

in combination with (i) gemcitabine or (ii) gemcitabine and erlotinib, for the treatment of pancreatic cancer in a human patient.

Another related aspect of the invention concerns the use of a compound represented by Formula I or Formula II as defined hereinabove for the manufacture of a medication for treating pancreatic cancer in a human patient in combination with (i) gemcitabine or (ii) gemcitabine and erlotinib.

The invention also relates to chemotherapeutic compositions comprising a compound represented by Formula I or Formula II as defined hereinabove, and a pharmaceutically acceptable carrier, wherein the composition is for use in treating pancreatic cancer in a human patient in combination with (i) gemcitabine or (ii) gemcitabine and erlotinib.

The invention further relates to a method of treating pancreatic cancer, the method comprising administering to a human patient in need thereof a pharmacologically effective amount of a compound represented by Formula I or Formula II as defined hereinabove in combination with (i) gemcitabine or (ii) gemcitabine and erlotinib. In one embodiment the compound represented by Formula I or Formula II is administered concurrently with administration of gemcitabine or concurrently with administration of gemcitabine and erlotinib. In another embodiment, the compound represented by Formula I or Formula II is administered before commencement of treatment cycles with gemcitabine or commencement of treatment cycles with gemcitabine and erlotinib. Advantageously, the administration of the compound represented by Formula I or Formula II is initiated upon diagnosis of pancreatic cancer in the human patient.

In some embodiments, n in Formula I or Formula II is 10, 8 or 6. The metallic monocationic counterion or dicationic counterion may be selected from the group consisting of sodium, potassium, calcium and magnesium. Preferably, the compound is a compound of Formula I in which X is sodium or potassium. Specific examples of compounds represented by Formula I or Formula II include, but are not limited to, capric acid, lauric acid, sodium caprate, sodium laurate, capric acid triglyceride (tricaprin), and lauric acid triglyceride (trilaurin).

In preferred embodiments, medium-chain length fatty acids such as capric acid and/or lauric acid are used in combination with chemotherapeutic agents such as gemcitabine, erlotinib, or both for the treatment of pancreatic cancer. According to those aspects, the use of medium-chain length fatty acids, salts or triglycerides thereof together with the first line therapy drug gemcitabine offers a significantly more efficacious treatment of pancreatic cancer. According to particular aspects of the invention, medium-chain length fatty acids, salts or triglycerides thereof display a significant antitumor activity against pancreatic cancer which synergizes with gemcitabine antitumor activity to provide an improved prognosis.

Further aspects of the invention will be apparent to a person skilled in the art from the following description, and claims and generalizations therein.

BRIEF DESCRIPTION OF THE DRAWINGS

In order that the invention may be readily understood, embodiments of the invention are illustrated by way of examples in the accompanying drawings.

DESCRIPTION OF SPECIFIC EMBODIMENTS

One novel approach to the treatment of pancreatic cancer lies in the discovery of compounds which are known to be relatively non-toxic but which possess previously unknown activity against pancreatic cancer or the combination of such compounds with gemcitabine which, when given together, are highly efficacious in treating tumor size and/or the spread of metastasis. Medium-chain length fatty acids, salts or triglycerides thereof administered along with gemcitabine may satisfy this requirement for a synergistic combination of compounds useful for the treatment of pancreatic cancer. That is, a combination of a medium-chain length fatty acid compound with gemcitabine which displays a synergistic anticancer activity offers a potential two-pronged approach for the treatment of a difficult and aggressive cancer to treat; pancreatic cancer. This two-pronged approach arises from the fact that use is made of two compounds with two distinct mechanisms of action; non-cytotoxic medium-chain length fatty acids, salts or triglycerides thereof combined with a cytotoxic drug, gemcitabine.

The present invention thus addresses two important limitations that arise with commonly used commercial chemotherapeutic agents, i.e. drug toxicity and drug resistance. Since medium-chain length fatty acids, salts or triglycerides thereof are significantly less toxic than standard chemotherapeutic drugs, including gemcitabine, the methods, compounds, and compositions should dampen chemotherapeutic drug resistance, especially for the treatment of pancreatic cancer in human patients.

Medium-chain length fatty acids refer to fatty acids containing eight to twelve carbon atoms. Therefore, medium-chain length fatty acids containing an even number of carbon atoms are C8 (octanoic acid or caprylic acid), C10 (decanoic acid or capric acid), and C12 (dodecanoic acid or lauric acid) fatty acids. These fatty acids are known to be very non-toxic compounds, especially when compared to chemotherapeutic drugs such as gemcitabine or kinase inhibitors such as erlotinib. For example, in *The Merck Index*, 11$^{th}$ Edition, page 266 (1989), caprylic acid is reported to have an $LD_{50}$ (oral, rats) =10.08 g/kg which is essentially not a toxic compound. In fact, according to part 184 of the Code of Federal Regulations (CFR), the US Food and Drug Administration has granted caprylic acid a GRAS (Generally Recognized as Safe) affirmation. Similarly, according to part 172 (CFR), free fatty acids (e.g., caprylic, capric, lauric) and their metallic salts are recognized as safe additives for use in food. As noted by Dimitrijevic et al. (J. Pharm. Pharmacol. 53:149-154, 2001), sodium decanoate is approved for human use in Japan and Sweden as an absorption enhancer for rectal drug products. Additionally, the triglycerides of medium-chain length fatty acids (e.g., three molecules of medium-chain length fatty acid esterified with one molecule of glycerol) have been established to be relatively non-toxic compounds safe for human use.

As indicated hereinbefore, there are some references which may suggest a link between medium-chain length fatty acids and antitumor activity. However, those references do not teach that the compounds of Formula I or Formula II can display a synergistic antitumor activity when used in combination with gemcitabine or gemcitabine and erlotinib, especially against an aggressive cancer such as pancreatic cancer. Indeed, it was unknown prior to the present invention that medium-chain length fatty acids such as caprylic acid, capric acid, lauric acid, metallic salts or triglycerides thereof may be effective for the treatment of pancreatic cancer. That discovery was completely unexpected since there are no precedents whereby a relatively non-toxic compound when used alone (e.g., capric acid, lauric acid) can display a significant antitumor activity in mammals against pancreatic cancer and subsequently can display a synergistic activity (e.g., caprylic acid, capric acid, lauric acid) when used along with gemcitabine. The lack of significant anticancer activity associated with medium-chain length fatty acid compounds is further supported by the fact that no cancer clinical trials have been reported to have been successfully undertaken with these compounds.

Although the present invention encompasses medium-chain length fatty acids having eight to twelve carbon atoms, their metallic salts (e.g., sodium, potassium, calcium, magnesium salts and other biocompatible earth metals), their triglyceride esters, and triesters of medium-chain length fatty acids with glycerol, it will be appreciated by anyone skilled in the art that certain structural modifications may fall within the scope of the invention. For example, an analogue of medium-chain length fatty acid triglycerides in which glycerol is replaced with serinol and so two molecules of medium-chain length fatty acids are esterified to the two hydroxyls of serinol and a third molecule of medium-chain length fatty acid is attached to the serinol amino function by an amide bond, constitutes an obvious example. Similarly, medium-chain length fatty acid di- and monoglycerides wherein two molecules and one molecule respectively of medium-chain length fatty acid(s) are esterified to glycerol provides other obvious examples. Finally, it will be appreciated by those skilled in the art that commercially available mixtures of medium-chain triglycerides (e.g., mixture of glycerol esters of C8 and C10 fatty acids in varying proportions) also constitute obvious examples. One example of such a commercial mixture of medium-chain triglycerides is the product, "Premium MCT Gold™" manufactured by Ultimate Nutrition Inc., Farmington, Conn. This product contains 67% tricaprylin and 33% tricaprin.

While it is possible that, for use in chemotherapy, the medium-chain length fatty acids, metallic salts or triglycerides thereof may be administered as the raw chemical either alone or with gemcitabine or with gemcitabine plus erlotinib, it is equally possible to present any of those active pharmaceutical ingredients as a pharmaceutical formulation or composition. These compositions include, but are not limited to, solids, liquids, oils, emulsions, gels, aerosols, inhalants, capsules, pills, patches, and suppositories.

A nontoxic composition is formed by the incorporation of any of the normally employed excipients such as, but not limited to, mannitol, lactose, trehalose, starch, magnesium stearate, talcum, cellulose, carboxymethyl cellulose, glucose, sucrose, gelatin, glycerol, magnesium carbonate, sodium citrate, sodium acetate, sodium chloride, sodium phosphate, and glycine. All methods include the step of bringing the active pharmaceutical ingredient(s) into association with the carrier which constitutes one or more accessory ingredients.

As used herein, the term "pharmaceutically acceptable" refers to drugs, medicaments, inert ingredients etc., which the term describes, suitable for use in contact with the tissues of humans without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans. The term "pharmaceutically acceptable vehicle" refers to a substance (e.g. a diluent, adjuvant, excipient, or carrier) with which a compound is administered, that substance not interfering with the physiological effects with the compounds of the invention, including but not limited to medium-chain length fatty acids such as capric acid or lauric acid, metallic salts or triglycerides thereof. The term "pharmaceutical composition" refers to at least one compound and at least one pharmaceutically acceptable vehicle, with which the compound is administered to a patient.

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder. In some embodiments, the term "treating" or "treatment" refers more particularly to cancers, including but not limited to pancreatic cancer, and encompasses any indicia of success in the treatment or amelioration of cancers-related pathology or conditions, including but not limited to slowing tumor growth, reduction of a tumor size, reduction of cancer cells proliferation, prevention or reduction of metastasis, increase of life expectancy or survival of patients having cancers, reducing toxicity chemotherapeutic drugs administered to a patient, etc. The term "treatment" or "treating" includes any therapy of existing pancreatic cancer, either at the site of the primary tumor (the pancreas) or metastasis to another organ, and prophylaxis of the cancer (e.g., metastasis from the pancreas to other organs) in a mammal. Reference herein to treatment extends to prophylaxis of cancers, and more particularly an established pancreatic cancer. Thus, for example, the compounds and compositions of the present invention could be used after surgical removal of a primary tumor, prior to surgery or prior to aggressive chemotherapy or even when the patient is in remission.

The capric or lauric acid, salts or triglycerides thereof of the present invention may be formulated using capric or lauric acid, salts or triglycerides thereof and pharmaceutically acceptable carriers by methods known to those skilled in the art (Merck Index, Merck & Co., Rahway, N.J.).

In one preferred embodiment, the pharmaceutical composition is in the form of any suitable composition for oral, sublingual, rectal, topical administration or inhalation (nasal spray), intramuscular, intradermal, subcutaneous, or intravenous administration for use in the treatment of pancreatic cancer.

The invention provides methods for the treatment of the aforementioned diseases comprising administration of a therapeutically effective amount of a compound of the invention or a composition comprising the same, to a subject, preferably a human subject, in need thereof. It will be appreciated that the amount of a composition of the invention required for use in the treatment will vary with the route of administration, the extent or stage of the pancreatic cancer being treated, the age and condition of the patient, and will ultimately be at the discretion of the attending physician. As used herein, "Therapeutically effective amount" or "pharmacologically effective amount" means the amount of compound that, when administered to a patient for treating a disease, is sufficient to effect such treatment of the disease. The "therapeutically effective amount" will vary depending on the compound, the disease and its severity, and the age, weight, etc., of the patient having the disease to be treated or prevented. The relative lack of toxicity of the compounds observed in the in vivo mouse studies (e.g., as observed in the attached examples) when compared to standard cancer therapies allows for a more liberal prophylactic use than would be advisable with standard therapies. The dose of compound in the combination therapy to be administered will ultimately be at the discretion of the oncologist. In general, however, the dose of medium-chain length triglycerides, metallic salts or triglycerides thereof in the combination regimen will be in the range from about 10 mg/kg to about 90 mg/kg per day. More preferably, the range will be between 30 mg/kg to 60 mg/kg per day. The desired dose may be conveniently presented in a single dose or as divided doses taken at appropriate intervals, for example as two, three or more doses per day as necessary to effect or bring about treatment of the patient's pancreatic cancer.

In another embodiment, the pharmaceutical composition is in a form suitable for enteral, mucosal (including sublingual, pulmonary and rectal), or parenteral (including intramuscular, intradermal, subcutaneous, and intravenous) administration. The formulations may, where appropriate, be conveniently presented in discrete dosage units and may be prepared by any of the methods well known in the art of pharmacy. All methods include the step of bringing into association the active pharmaceutical ingredient with liquid carriers or finely divided solid carriers or both and then, if necessary, shaping the product into the desired form. When desired, the above-described formulations adapted to give sustained release of the active pharmaceutical ingredient may be employed. Sustained release formulations well known to the art include biocompatible polymers (e.g., enteric coating of the active pharmaceutical ingredient to avoid any stomach upset), liposomes, bolus injection, or continuous infusion.

In certain embodiments, the compounds and composition according to the invention can be used in combination therapy with at least one other chemotherapeutic drug. In certain embodiments, the compounds of the invention can be administered concurrently with the administration of another chemotherapeutic drug. In certain embodiments, the compounds of the invention can be administered prior or subsequent to administration of another chemotherapeutic drug. The at least one other chemotherapeutic drug be effective for treating the same or different disease, disorder, or condition (e.g. pancreatic cancer). Methods of the present invention include administration of one or more compounds or pharmaceutical compositions of the present invention and one or more other chemotherapeutic drugs provided that the combined administration does not inhibit the therapeutic efficacy of the one or more compounds of the present invention and/or does not produce adverse combination effects.

In certain embodiments, compositions of the present invention can be administered concurrently with the administration of another chemotherapeutic drug, which can be part of the same pharmaceutical composition as, or in a different composition from, that containing the compounds of the present invention. In certain embodiments, compounds of the present invention can be administered prior or subsequent to administration of another chemotherapeutic drug. In certain embodiments of combination therapy, the combination therapy comprises alternating between administering a composition of the present invention and a composition comprising another chemotherapeutic drug, e.g., to minimize adverse side effects associated with a particular drug. When a compound of the present invention is administered concurrently with another chemotherapeutic drug that potentially can produce adverse side effects including, but not limited to, toxicity, the chemotherapeutic drug can advantageously be administered at a dose that falls below the threshold at which the adverse side effect is elicited.

In certain embodiments, a pharmaceutical composition can further comprise substances to enhance, modulate and/or control release, bioavailability, therapeutic efficacy, therapeutic potency, stability, and the like. For example, to enhance therapeutic efficacy of a compound of the present invention, the compound can be co-administered with one or more active agents to increase the absorption or diffusion of the compound from the gastrointestinal tract, or to inhibit degradation of the drug in the systemic circulation. In certain embodiments, at least one compound of the present invention can be co-administered with active agents having a pharmacological effect that enhance the therapeutic efficacy of a compound of Formula I or Formula II (e.g. capric acid, lauric acid, sodium caprate, sodium laurate, capric acid triglyceride (tricaprin) and lauric acid triglyceride (trilaurin)).

For instance, according to a particular embodiment of this invention applied to chemotherapy, capric or lauric acid, salts or triglycerides thereof can be administered prior to, during, or subsequent to the chemotherapy (e.g., prior to, during, and/or subsequent to the administration of gemcitabine and/or erlotinib or any other cytotoxic agent which may be appropriate for the treatment of pancreatic cancer).

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference. The invention is further illustrated by the following examples, which should not be construed as further limiting.

EXAMPLES

The Examples set forth herein below provide exemplary uses of certain representative compounds of the invention. Also provided are exemplary methods for assaying the compounds of the invention for in vitro cytotoxicity and in vivo efficacy.

Example 1

In Vitro Cytotoxicity of Compounds Assayed on Pancreatic Cancer Cells

This assay was performed to determine the effect of compounds of the present invention on cell cytotoxicity. Panc02 cells were incubated in presence or absence of compounds in RPMI-1640 conditioned media. After 24 hours incubation, 50 μl of 3-(4,5-dimethyl-2-thiazyl)-2,5-diphenyl-2H-tetrazolium bromide (MU; 2 mg/ml) was added and further incubated for 4 hours. The supernatant was discarded and 100 μl of dimethylsulfoxide (DMSO) was added. Absorbance was read at 570 nm with an ELISA Tecan Sunrise plate reader. The control group consisted of cells without compounds and is referred to as 100% of viable cells. $IC_{50}$ was determined using Prism software. Table 1 represents the effect ($IC_{50}$) of compounds on pancreatic cancer cells (Panc02) in a 24-hour cell culture.

TABLE 1

Effect of selected compounds on pancreatic (Panc02) cancer cell cytotoxicity in 24 h cell cultures.

| Compounds | $IC_{50}$ (mM) |
| --- | --- |
| Decanoic acid | 0.63 |
| Sodium decanoate | 0.52 |
| Sodium dodecanoate | 0.15 |

As can be appreciated, all three compounds tested have antitumor activity against Panc02 cells.

Example 2

Anti-Tumor Efficacy Validation of Sodium Decanoate in Combination with Gemcitabine in the Panc02 Mouse Pancreatic Cancer Model The syngeneic Panc02 is a pancreatic adenocarcinoma tumor cell line obtained from NCI (0507232). Panc02 cells are positive for Ki-Ras, p53, HerNEU and CDK. Panc02 were grown in RPMI-1640 containing 10% fetal bovine serum. At day 0, 50 μl of 7.5×10⁵ viable Panc02 cells were intradermally injected to produce localized tumors in 6- to 8-week old C57BL/6 mice. The animals were then serially monitored by manual palpation for evidence of tumor. Mice were then treated every day with oral administration of vehicle (negative control), or sodium decanoate and with intraperitoneal injection of gemcitabine (50 mg/kg) at day 21, 28, 35 and 42. Mice were sacrificed between days 36 to 50. Serial tumor volume was obtained by bi-dimensional diameter measurements with calipers, using the formula 0.4 (a×b²) where "a" was the major tumor diameter and "b" the minor perpendicular diameter. Tumors were palpable, in general, 3-5 days post-inoculation. Percentage of tumor growth is reported as the percentage of growth of the pancreatic tumor on a given day relative to that growth which is observed on the first day of treatment with medium-chain length fatty acid, or sodium salt or triglyceride or vehicle (control). T/C is defined as: Treated Tumor Growth CYO/Control Tumor Growth (%).

Figure 1:
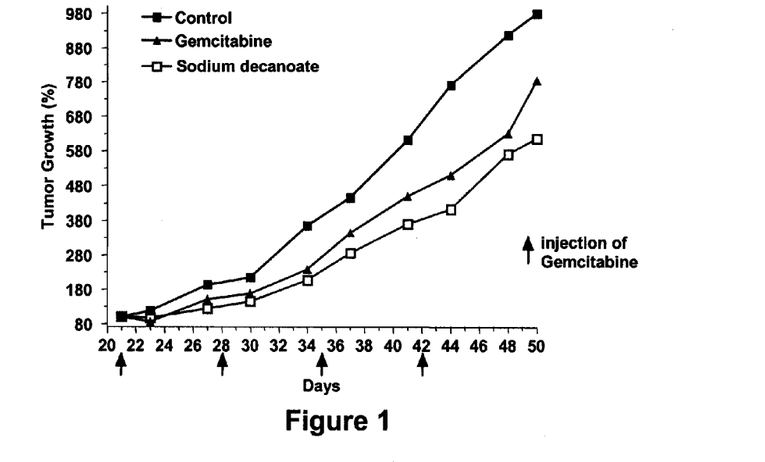
FIG. 1 is a line graph showing the effects of oral administration of sodium decanoate and gemcitabine on syngeneic Panc02 pancreas tumor growth in mice.

FIG. 1 represents the antitumor efficacy of oral administration of sodium decanoate (100 mg/kg) and gemcitabine (i.v., 50 mg/kg) in pancreatic Panc02 cancer. Gemcitabine induces a significant inhibition (p<0.05) of tumor growth from day 27 to 34 with a T/C from 55 to 78%. Sodium decanoate induces a significant inhibition (p<0.05) of tumor growth from day 23 to 44 with a T/C from 26% to 58%. This inhibition is comparable with that which is observed with gemcitabine.

Figure 2:
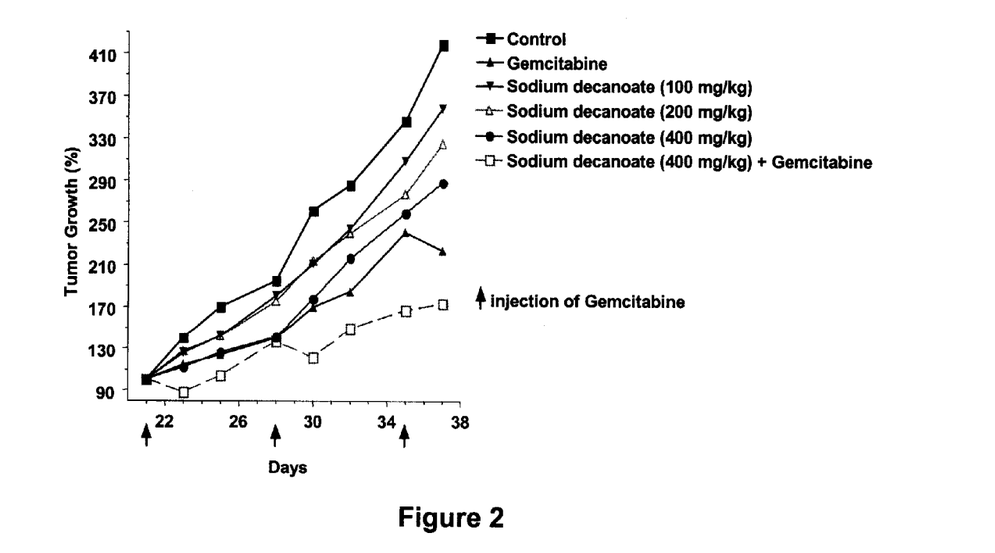
FIG. 2 is a line graph showing the effects of oral administration of sodium decanoate and combination of sodium decanoate with gemcitabine on syngeneic Panc02 pancreas tumor growth in mice.

FIG. 2 shows the antitumor efficacy of oral administration of sodium decanoate (100, 200 and 400 mg/kg) and combination of gemcitabine (iv) with sodium decanoate (oral) in pancreatic Panc02 cancer. Gemcitabine induces a significant (p<0.05) inhibition of tumor growth from day 23 to 37. A T/C<40% was observed at day 23, 25 and 37. Sodium decanoate induces a significant (p<0.05) inhibition of the tumor growth in a dose dependent fashion. A significant p value (p<0.05) compared to control in tumor growth inhibition was observed from day 23 to 37 when used at a concentration of 400 mg/kg of sodium decanoate. A T/C<40% was observed at day 23 and 25. The combination regimen (gemcitabine+sodium decanoate, 400 mg/kg) induces a significant p value (p<0.05) inhibition of the tumor growth and a T/C<40% from day 23 to 37. The inhibition of tumor growth induced by the combination therapy was significant (p<0.05) compared to gemcitabine alone at day 23, 25 and 30 to 39. Mice were sacrificed at day 37.

FIG. 2 shows that a significant antitumor effect is observed with the combination of gemcitabine, the standard drug, and sodium decanoate relative to gemcitabine alone. Furthermore, this significant anticancer effect is the result of an unanticipated or synergistic effect between gemcitabine and sodium decanoate because without a synergistic activity, statistical significance would not be observed. Additionally, use of an increased concentration of gemcitabine does not replicate this activity since mortality is observed.

Figure 3:
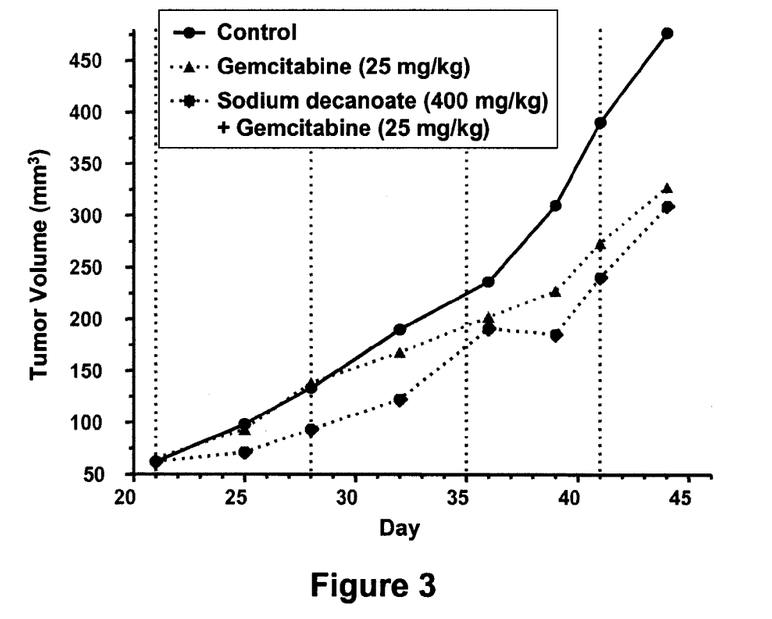
FIG. 3 is a line graph showing the effects of oral administration of sodium decanoate with sub-therapeutic dose of gemcitabine (ip, 25 mg/kg) on syngeneic Panc02 tumor volume in mice.

FIG. 3 represents the antitumor effect of sodium decanoate in combination with a sub-therapeutic dose of gemcitabine (25 mg/kg) in pancreatic Panc02 cancer from day 21 to 32. Gemcitabine at 25 mg/kg induces a significant inhibition (p<0.05) of tumor growth at day 39 with no therapeutic activity (T/C>40). Combination of sodium decanoate with gemcitabine at 25 mg/kg induces a significant inhibition (p<0.05) of tumor growth from day 25 to 44 with a T/C<40 at day 25 and 28. Furthermore, the inhibition of tumor growth induced by the combination therapy (sodium decanoate+gemcitabine 25 mg/kg) was significant (p<0.05) compared to gemcitabine alone at day 25 to 32. This data indicates clearly the synergistic activity between gemcitabine and sodium decanoate from day 25 to 32.

Unlike the example described in FIGS. 1 and 2, animals treated with PBI-1402 or gemcitabine alone did not display anticancer activities in the early phase of the treatment. The lack of activity in this experiment (FIG. 3) probably reflects a less aggressive growth of the tumor up to day 36, followed by an exponential growth from day 36 to 45 where gemcitabine displays anticancer activity.

Figure 4:
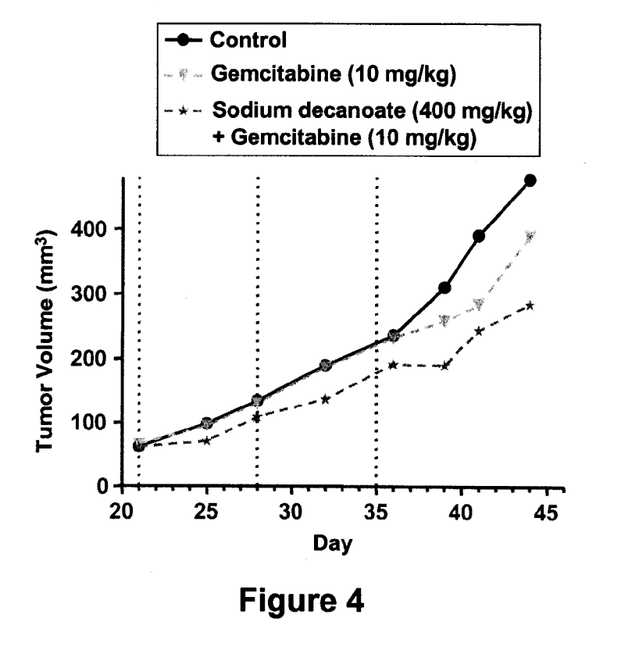
FIG. 4 is a line graph showing the effects of oral administration of sodium decanoate with sub-therapeutic dose of gemcitabine (ip, 50 mg/kg) on syngeneic Panc02 tumor volume in mice.

FIG. 4 represents the antitumor effect of sodium decanoate in combination with a sub-therapeutic dose of gemcitabine (10 mg/kg) in pancreatic Panc02 cancer from day 21 to 36. Gemcitabine at 10 mg/kg induces a significant inhibition (p<0.05) of tumor growth at day 41 with no T/C<40. The combination of sodium decanoate with gemcitabine at 10 mg/kg induces a significant inhibition (p<0.05) of tumor growth at day 25, 32 and 39 to 44 with a T/C<40 at day 25. Furthermore, the inhibition of tumor growth induced by the combination therapy (sodium decanoate+gemcitabine 10 mg/kg) was significant (p<0.05) compared to gemcitabine alone at day 25 and 36. This data indicates clearly the synergistic activity between gemcitabine and sodium decanoate from day 25 to 36.

Unlike the example described in FIGS. 1 and 2, animals treated with PBI-1402 or gemcitabine alone did not display anticancer activities in the early phase of the treatment. The lack of activity in this experiment (FIG. 4) probably reflect a less aggressive growth of the tumor up to day 36, followed by an exponential growth from day 36 to 45 where gemcitabine displays anticancer activity.

Example 3

Anti-Tumor Efficacy Validation of Sodium Decanoate in Combination with Gemcitabine in the Panc02 Mouse Orthotopic Pancreatic Cancer Model At day 0, 50 µl of $1 \times 10^6$ viable Panc02 cells per ml were injected onto the pancreas to produce orthotopic tumors in 6- to 8-week old C57BL/6 mice. Mice were then treated every day with oral administration of vehicle (negative control), or sodium decanoate and with intraperitoneal injection of gemcitabine (50 mg/kg) once a week (day 1, 8, 15, etc.). The experimental endpoint (death) was defined as the time point at which mice developed a distended abdomen due to ascites or exhibited moribund behavior, at which time the animals were euthanized and examined.

Figure 5:
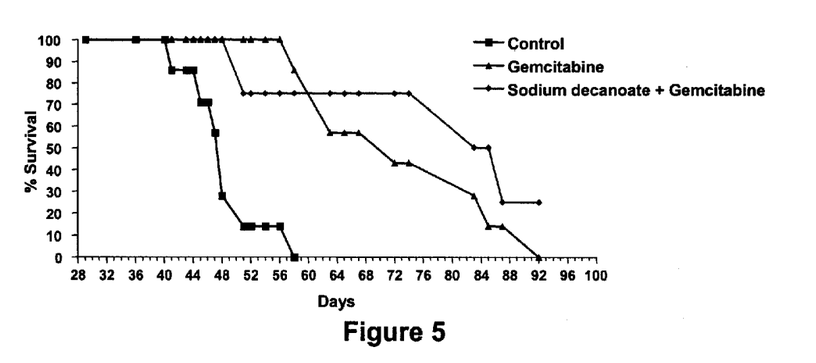
FIG. 5 is a line graph showing the effects of oral administration of sodium decanoate in combination with gemcitabine on mice survival with orthotopic syngeneic Panc02 pancreatic tumor.

After orthotopic injection of Panc02 cells onto the pancreas, all animals develop tumors that were palpable. Mice developed ascites with abdominal metastases. Metastases were mostly observed in liver, bile duct, spleen, diaphragm, and mesenteries. FIG. 5 shows the antitumor efficacy of oral administration of sodium decanoate (200 mg/kg) in combination with gemcitabine (i.v.) compared to gemcitabine alone in the orthotopic pancreatic Panc2 cancer model. Mice treated with gemcitabine and a combination of gemcitabine and sodium decanoate showed prolonged survival compared with mice that had received vehicle (control). Median survival was 71 days for gemcitabine-treated mice compared with 48 days in control mice. Gemcitabine-treated mice who had received sodium decanoate survived a median of 88 days.

Table 2 represents the percent survival of mice in control versus treated groups. At day 58, no survival was observed in the control group, compared to 86% and 75% survival in gemcitabine- and gemcitabine+sodium decanoate-treated group, respectively. From day 72 up to day 87, treatment with the combination therapy (gemcitabine+sodium decanoate) induces close to twice the survival of mice compared to gemcitabine alone. At day 92, all mice are dead in the gemcitabine-treated group compared with 25% survival observed in gemcitabine+sodium decanoate-treated group. The remaining mice in the combination therapy are still alive after 100 days of treatment.

TABLE 2

Effect of oral administration of sodium decanoate in combination with gemcitabine on survival of mice.

| Days | Groups | % Survival |
| --- | --- | --- |
| 58 | Control | 0 |
|  | Gemcitabine | 86 |
|  | Gemcitabine + sodium decanoate | 75 |
| 72 | Control | 0 |
|  | Gemcitabine | 42 |
|  | Gemcitabine + sodium | 75 |

TABLE 2-continued

Effect of oral administration of sodium decanoate in combination with gemcitabine on survival of mice.

| Days | Groups | % Survival |
|---|---|---|
| 83 | Control | 0 |
|  | Gemcitabine | 28 |
|  | Gemcitabine + sodium decanoate | 50 |
| 87 | Control | 0 |
|  | Gemcitabine | 14 |
|  | Gemcitabine + sodium decanoate | 25 |
| 92 | Control | 0 |
|  | Gemcitabine | 0 |
|  | Gemcitabine + sodium decanoate | 25 |

Example 4

Anti-Tumor Efficacy Validation of Sodium Dodecanoate in Combination with Gemcitabine in the Panc02 Mouse Pancreatic Cancer Model The effect of sodium dodecanoate and gemcitabine in pancreatic Panc02 cancer was determined as described in Example 2.

Figure 6:
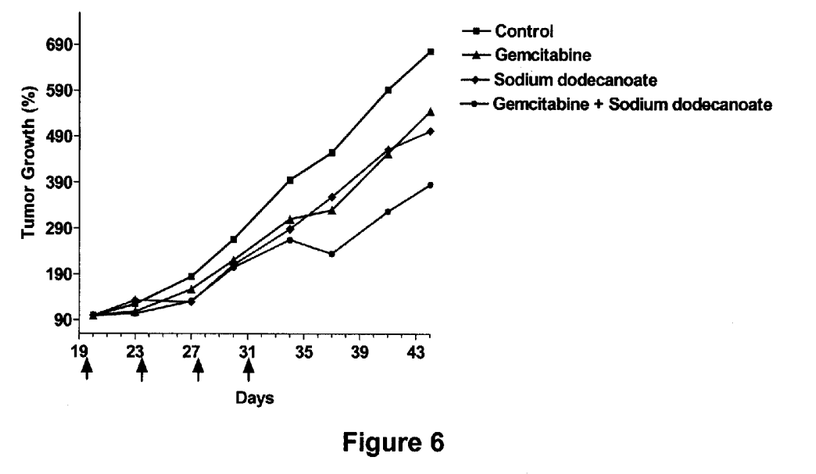
FIG. 6 is a line graph showing the effects of oral administration of sodium dodecanoate and gemcitabine on syngeneic Panc02 pancreas tumor growth in mice.

FIG. 6 represents the antitumor efficacy of oral administration of sodium dodecanoate (200 mg/kg) and gemcitabine (i.v., 50 mg/kg) in pancreatic Panc02 cancer. Gemcitabine induces a significant inhibition ($p<0.05$) of tumor growth at day 44 with a T/C from 64% to 77%. Sodium dodecanoate induces a significant inhibition ($p<0.05$) of tumor growth at day 44 with a T/C from 64% to 74%. The combination regimen (gemcitabine+sodium dodecanoate, 200 mg/kg) induces a significant ($p<0.05$) inhibition of the tumor growth and a T/C<40% from day 16 to 44.

FIG. 6 shows that a significant antitumor effect is observed with the combination of gemcitabine, the standard drug, and sodium dodecanoate relative to gemcitabine alone. Furthermore, this significant anticancer effect is the result of an unanticipated or synergistic effect between gemcitabine and sodium dodecanoate because without a synergistic activity, statistical significance would not be observed. Additionally, use of an increased concentration of gemcitabine does not replicate this activity since mortality is observed.

Example 5

Anti-Tumor Efficacy Validation of Tricaprin in Combination with Gemcitabine in the Panc02 Mouse Orthotopic Pancreatic Cancer Model The effect of gemcitabine and tricaprin in combination with gemcitabine in orthotopic pancreatic Panc02 cancer was determined as described in Example 3.

Figure 7:
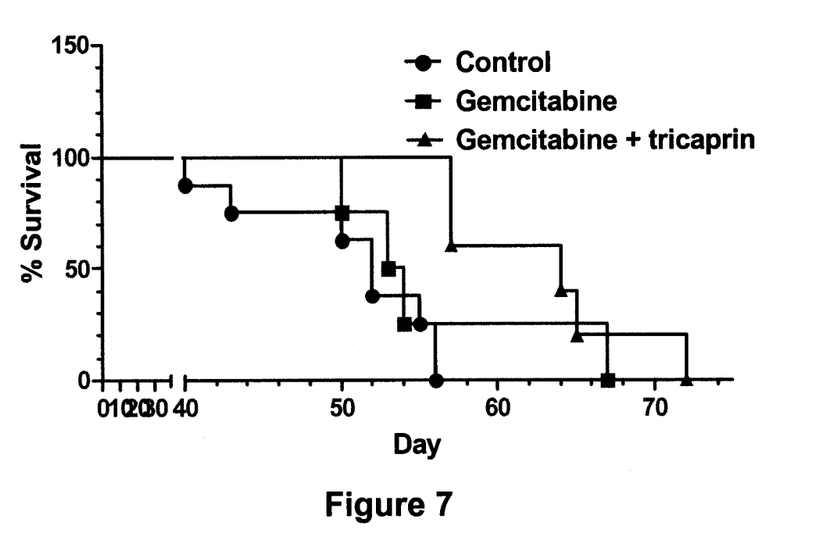
FIG. 7 is a line graph showing the effects of oral administration of tricaprin in combination with gemcitabine on survival of mice with orthotopic syngeneic Panc02 pancreatic tumor.

FIG. 7 shows the antitumor efficacy of oral administration of tricaprin (600 mg/kg) in combination with gemcitabine (i.v., 50 mg/kg) compared to gemcitabine alone in the orthotopic pancreatic Panc2 cancer model. Mice treated with gemcitabine and a combination of gemcitabine and tricaprin displayed prolonged survival compared with mice that had received vehicle (control). Median survival was 53.5 days for gemcitabine-treated mice compared with 52 days in control mice. Gemcitabine-treated mice who had received tricaprin survived a median of 64 days.

All technical and scientific terms used herein have the same meaning as commonly understood by one ordinary skilled in the art to which the invention pertains. For convenience, the meaning of certain terms and phrases used herein are provided.

To the extent the definitions of terms in the publications, patents, and patent applications incorporated herein by reference are contrary to the definitions set forth in this specification, the definitions in this specification control. The section headings used herein are for organizational purposes only, and are not to be construed as limiting the subject matter disclosed.

It should be noted that, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

The invention claimed is:

1. A method of treating pancreatic cancer, said method comprising administering to a human patient in need thereof a pharmacologically effective amount of a compound represented by Formula I or Formula II:

wherein n is 8 and X is hydrogen, a metallic monocationic counterion or a dicationic counterion;
in combination with (i) gemcitabine or (ii) gemcitabine and erlotinib;
wherein said gemcitabine is administered at a subtherapeutic dosage.

2. The method of claim 1, wherein the metallic monocationic counterion or dicationic counterion is selected from the group consisting of sodium, potassium, calcium and magnesium.

3. The method of claim 1, wherein the compound to be administered is a compound of Formula I in which X is sodium or potassium.

4. The method of claim 1, wherein the compound to be administered is capric acid.

5. The method of claim 1, wherein the compound to be administered is sodium caprate.

6. The method of claim 1, wherein the compound to be administered is capric acid triglyceride (tricaprin).

7. The method of claim 1, wherein the compound represented by Formula I or Formula II is administered concurrently with administration gemcitabine or concurrently with administration of gemcitabine and erlotinib.

8. The method of claim 1, wherein the compound represented by Formula I or Formula II is administered before commencement of treatment cycles with gemcitabine or commencement of treatment cycles with gemcitabine and erlotinib.

9. The method of claim 8, wherein administration of the compound represented by Formula I or Formula II is initiated upon diagnosis of pancreatic cancer in said human patient.

10. A method for treating pancreatic cancer in a human patient in need thereof, the method comprising administering to said patient:

(a) a compound represented by Formula I or Formula II:

wherein n is 8 and X is hydrogen, a metallic monocationic counterion or a dicationic counterion; and (b) at least one (i) gemcitabine or (ii) gemcitabine and erlotinib;

wherein (a) and (b) are administered according to a dosage regimen providing a synergistic antitumor activity.

11. The method of claim 10, wherein the metallic monocationic counterion or dicationic counterion is selected from the group consisting of sodium, potassium, calcium and magnesium.

12. The method of claim 10, wherein the compound of Formula I is capric acid.

13. The method of claim 10, wherein the compound of Formula I is sodium caprate.

14. The method of claim 10, wherein the compound of Formula I is capric acid triglyceride (tricaprin).

* * * * *